United States Patent [19]

McCrudden et al.

[11] 4,134,850
[45] Jan. 16, 1979

[54] BLEACHING COMPOSITION

[75] Inventors: Joseph E. McCrudden, Warrington; Robert E. Talbot, Burtonwood, both of England

[73] Assignee: Interox Chemicals Limited, London, England

[21] Appl. No.: 683,811

[22] Filed: May 6, 1976

[30] Foreign Application Priority Data

Dec. 23, 1975 [GB] United Kingdom ............... 52520/75

[51] Int. Cl.² ...................... C11D 3/395; C11D 7/54; D06L 3/02
[52] U.S. Cl. .................................... 252/186; 8/111.5; 252/95; 252/99; 568/563; 568/559
[58] Field of Search ........................... 252/186, 95, 99; 260/502 R, 610 R, 610 A; 8/111.5

[56] References Cited

U.S. PATENT DOCUMENTS

| 2,795,618 | 6/1957 | Emerson et al. | 252/186 |
| 3,211,773 | 10/1965 | Lederer | 252/186 |
| 3,538,011 | 11/1970 | van der Klaauw | 252/186 |
| 3,574,519 | 4/1971 | Lincoln et al. | 252/186 |

Primary Examiner—Benjamin R. Padgett
Assistant Examiner—Irwin Gluck
Attorney, Agent, or Firm—Larson, Taylor and Hinds

[57] ABSTRACT

The present invention provides bleaching or detergent compositions containing a cycloaliphatic peroxyacid of general formula:

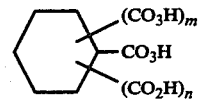

wherein
$0 \leq m \leq 5$,
$0 \leq n \leq 5$ and
$n + m \geq 1$,
and mono or diethylenically unsaturated derivatives thereof, and processes for washing/bleaching using such peroxyacids, preferably at a temperature of from 30 to 60° C. The peroxyacids can be generated in situ by hydrolysis or perhydrolysis of the corresponding diacyl peroxide. The peroxyacid and diacyl peroxide can be desensitized by intimate contact with a diluent e.g. lauric acid or magnesium sulphate and coated to reduce destructive interaction with other components of the detergent or bleaching composition.

13 Claims, No Drawings

BLEACHING COMPOSITION

The present invention relates to bleaching compositions and to processes for bleaching.

According to the present invention there is provided a process for bleaching with an aqueous solution of an aliphatic peroxyacid having general formula:

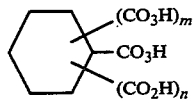

wherein m and n each represent an integer of from 0 to 5, provided n + m ≧ 1 or mono- or diethylenically unsaturated derivatives thereof, or an anion thereof.

According to a second aspect of the present invention there is provided a bleaching composition or detergent composition containing (a) an aliphatic peroxyacid having general formula:

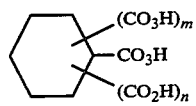

wherein m and n each represent an integer of from 0 to 5, provided n + m ≧ 1 or mono- or diethylenically unsaturated derivatives thereof, or an anion thereof, or (b) a precursor of the aliphatic peroxyacid, and if necessary a donor of perhydroxyl anions.

Optionally the peroxyacid or precursor thereof can be substituted by a lower alkyl, chloro or nitro group.

According to a third aspect of the present invention there is provided a composition suitable for mixing with a surfactant and optionally other conventional components to form a heavy duty washing composition (a) an aliphatic peroxyacid having general formula:

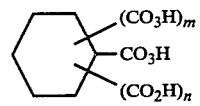

wherein m and n each represent an integer of from 0 to 5, provided n + m ≧ 1 or mono- or diethylenically unsaturated derivatives thereof, or an anion thereof, or (b) a precursor of the aliphatic peroxyacid, and if necessary a donor of perhydroxyl anions, mixed with a detergent builder and/or a processing additive and optionally components of heavy duty washing compositions other than the surfactant.

The peroxyacid can be generated in solution by hydrolysis or perhydrolysis of the precursor. One class of favoured precursors comprises acyl peroxides, from which peracids can be generated by both hydrolysis and perhydrolysis.

It will be recognised that, depending upon the presence or absence of other substituents, m + n can vary between 1 and 5. Conveniently, when n = 1 and m = 0, the compound is the monoperoxyacid and when m = 1 and n = 0 a preferable arrangement, the compound is the diperoxyacid analogue of cyclohexane-1,2- or -1,3-or -1,4-dicarboxylic acid, or of the corresponding mono- or di-ethylenically unsaturated derivatives such as 1- or 4-cyclohexene-1,2-dicarboxylic acid, and 2,5-cyclohexdiene-1,4-dicarboxylic acid. Many of the dicarboxylic acids contain at least one assymetric carbon atom so that the peroxyacids can be cis or trans, and in some cases contain optically active forms. Many preparations result in mixtures. In other embodiments m + n is 2, for example peroxy derivatives of cyclohexane-1,2,3-, -1,2,4- or -1,3,5-tricarboxylic acids, and corresponding ethylenically unsaturated compounds such as 1-cyclohexene-1,3,5-tricarboxylic acid. In still other embodiments m + n is 4, for example peroxy derivatives of cyclohexane-1,2,3,4-, -1,2,3,5- or -1,2,4,5-tetracarboxylic acid, or n is 5, i.e. peroxy derivatives of cyclohexane-1,2,3,4,5,6-hexacarboxylic acid.

It will be recognised that some of the peroxycompounds contain at least one moiety containing two or more carboxy or peroxycarboxy groups in 1, 3 or 1,4 positions. In consequence, to at least some extent, unless specific precautions are taken, production of diacyl peroxides can lead to formation of polymeric acyl peroxides, i.e. compounds containing at least two acyl peroxide linkages, especially if the moiety intentionally contains more than one peroxide group. Since such polymeric acyl peroxides also form the requisite peroxyacids in aqueous solution, they are included within the present invention. It will also be recognised that others of the peroxy compounds contain two vicinal peroxycarboxy groups. Unless specific precautions are taken during their production, there can be a tendency for internal acyl peroxides to be formed to at least some extent. Such peroxides can form the requisite peroxyacids by perhydrolysis in the same way as diacyl peroxides, and thus are encompassed within the present invention.

In some embodiments the alicyclic peroxyacids preferably contain more than one peroxyacid group, and advantageiously do not contain carboxy groups, because, in general, such a preferred arrangement allows a given amount of active oxygen to be provided in a smaller amount of alicyclic compound, and secondly absence of carboxy groups seems to result in more efficient use of the active oxygen for bleaching.

Although we do not wish to be bound by any theory, we believe that the electrostatic repulsion between the bleaching species can be electrostatically repelled by the negatively chared fabric surface. Carboxy groups have in general a much lower pKa than peroxycarboxy groups, and hence at any given pH a higher proportion of carboxy groups will be ionised than is the case for the corresponding peroxycarboxy groups. Thus, the tendency for the molecule to be negatively chared increases as the proportion of carboxy groups increases, and hence the degree of repulsion between bleaching species and fabric increases.

As referred to hereinbefore, favoured precursors of the peroxyacids are the corresponding acyl peroxides. Depending upon the conditions employed, diacyl peroxides e.g. 2,2'-dicarboxy cyclohexanoyl peroxide, or internal acyl peroxides, e.g. bicyclo(4,4,0)-2,3-dioxadecane-1,4-dione, can be formed.

Other suitable diacyl peroxides include 3,3'-dicarboxy-, 3,3'-diperoxycarboxy-, 4,4'-dicarboxy-, and 4,4'-diperoxycarboxydicyclohexanoyl peroxide, 2,2'-dicarboxy and 2,2'-diperoxycarboxydicyclohex-1-enoyl peroxide, 2,2'-dicarboxy-, and 2,2'-diperoxycarboxydicyclohex-4-enoyl peroxide and 4,4'-dicarboxy and 4-4'-diperoxycarboxydicyclohex-2-5-dienoyl peroxide, when n is 1. When n is 2, suitable peroxides include 2,2',3,3'-tetracarboxy-, 2,2',3,3'-tetraperoxycarboxy-, 2,2',4,4'-tetracarboxy-, and 2,2',4,4'-tetraperoxycarboxy-, 3,3',5,5'-tetracarboxy-, and 3,3',5,5'-tetraperoxycarboxydicyclohexanoyl peroxide and 3,3',5,5'-tetracarboxy-, and 3,3',5,5'-tetraperoxycarboxydicyclohex-1-enoyl peroxide. When n is 3 suitable peroxides include 2,2',3,3',4,4'-hexacarboxydicyclohexanoyl peroxide and when n is 5, 2,2',3,3',4,4',5,5',6,6'-decacarboxydicyclohexanoyl peroxide.

If desired asymmetric peroxides, based on the moieties employed in the symmetric peroxides aforementioned, can be used. The other moiety completing the diacyl peroxide can be one of the remaining moieties aforementioned, or any other compatible acyl group. Compatible groups can be aromatic such as phthaloyl, isophthaloyl, terephthaloyl, trimesoyl or pyromellitoyl or the corresponding groups in which the carboxy group or groups is n are replaced by a peroxycarboxy group or groups, the aromatic groups optionally being substituted by lower alkyl, chloro or nitro groups. Where aqueous solubility is less important, the aromatic group can also be benzoyl, optionally substituted by lower alkyl, chloro or nitro groups. Compatible groups can also be aliphatic, such as acetyl, succinyl and glutaryl.

Aliphatic peroxyacids and their peroxide derivatives described herein suffer to a certain extent from a tendency to lose their active oxygen content when they are subjected to shock, elevated temperatures or abrasion, under some circumstances sufficiently rapidly to result in detonation or explosion. In consequence, according to a further aspect of the present invention there are provided compositions in which the peroxyacid or peroxide described hereinbefore has been desensitised with a desensitisng amount of a solid desensitising diluent, e.g. brought into contact with sufficient diluent to render the composition non-hazardous in and as measured by the standard drop weight test described hereinafter. In a standard drop weight test, 30 mg of material, which has been sieved to finer than 710 microns, is placed on an anvil in the apparatus. The anvil is centred and the sample tamped lightly by a force of 5 Kg-cm. A weight is then dropped several times from a given height, each time onto a fresh sample, and its effect observed. A positive result can range from being merely a discoloured product, through emission of a cloud of smoke, to, in an extreme case, an explosion. Tests are carried out at a series of heights. A higher proportion of positive results occur when a greater impact is employed. The figure usually quoted is the median point, E50 i.e. the point at which 50% of the results at a given impact are positive. Compositions having a median point of at least 200 kg-cm are considered to be non-hazardous in the test, but to provide a greater margin of safety compositions preferably have a median point of at least 300 Kg-cm.

Generally the desensitising amount is selected within the range of 1 to 10 parts by weight of diluent per part of bleaching agent. Suitably the desensitising diluent can be selected from hydrocarbons having melting points in excess of 30° C., e.g. microcrystalline waxes, aliphatic fatty acids, e.g. lauric and stearic acids, aromatic acids e.g. benzoic acid, alkyl esters of the aliphatic or aromatic acids, e.g. t-butyl stearate, protein or starch materials, boric acid, aluminium sulphate, clays, aluminosilicates, and especially alkali and alkaline earth metal salts of halogen-free acids having a first dissociation constant of at least $1 \times 10^{-3}$, e.g. sodium sulphate, magnesium sulphate and sodium tripolyphosphate. Sodium sulphate is an example of a processing aid and sodium tripolyphosphate is an example of a detergent builder. The intimate contact can be by way of admixing particles of the diluent with the alicyclic peroxyacid or peroxide or by granulating or coating the alicyclic peroxyacid or peroxide with the diluent. More than one diluent may be employed, conveniently first contacting the alicyclic peroxyacid or peroxide with an unreactive diluent described hereinbefore, and then coating the mixture with a second diluent. Such second diluent can be selected from fatty acid alkanolamides, fatty alcohol polyglycol ethers, polyglycol and polypropylene oxide polymers, alkaryl polyglycol ethers, polyethylene glycol and fatty acid esters and, amides thereof, and esters and amides of glycerol and sorbitol, polyvinyl alcohol, polymethyl methacrylate, dextrin, starch, gelatin carboxymethyl methacrylate, solid hydrocarbons, aliphatic fatty acids, fatty alcohols, sodium sulphate and magnesium sulphate. "Fatty" in the terms "fatty alcohol" and "fatty acid" is used to denote at least 12, desirably from 12 to 26 carbon atoms in the longest chain. Normally the amount of coating is within the range of 3% to 35% by weight based on the weight of the coated product. Alicyclic peroxyacid or peroxide thus coated is less prone to decomposition when stored in contact with alkaline surfactants, such as sodium salts or alkyl benzene sulphonates, which are commonly employed in detergent and bleaching compositions. Where peroxyacid precursors other than aycl peroxides are employed, they can be treated in the same way as acyl peroxides if they contain active oxygen they preferably are isolated from other components of the composition by the water soluble or dispersible coating described hereinbefore.

As referred to hereinbefore certain precursors require perhydroxyl anions to generate peroxyacids. The perhydroxyl anions can be provided by separate addition of hydrogen peroxide or any inorganic active oxygen containing compounds hereinafter called persalts such as sodium perborate or sodium percarbonate (the hydrogen peroxide addition product). Preferably the bleaching composition of the detergent composition or the composition for mixing with a surfactant contains the persalt in addition to the precursor, advantageously in a mole ratio of from 5:1 to 1:5, particularly in a mole ratio of approximately 1:1, of persalt to precursor, on the assumption that the precursor contains one perhydrolysable site per molecule. Each acyl peroxide linkage forms a polymerisable site. Where each precursor molecule contains more than one such perhydrolysable site then the ratio of persalt to precursor is preferably increased "pro rata". By way of clarification a diacyl peroxide contains one such site, but a polymeric acyl peroxide contains a plurality of such sites.

Generally bleaching solutions according to the present invention contain at least 1 ppm available oxygen "av ox" and for use in washing textile fabrics, e.g. cotton or cotton/polyesters often from 5 to 200 ppm "av ox". Solutions for cleaning surfaces such as metal, plastic or wooden surfaces often contain from 200 ppm to 500 ppm "av ox". If desired, solutions produced by the dissolution of compositions described herein can be used to bleach textile fabrics, wood or pulp under the conditions, and employing the equipment used for bleaching such articles with hydrogen peroxide or inorganic peroxoacids.

Suitably, bleaching/washing in the home can take place at ambient temperature or higher, conveniently in the range of 25° to 60° C. In general, the bleaching and detergent compositions are each formulated to produce solutions having a pH of between 8.5 and 11.5; preferably from 8.5 to 9.5.

Generally speaking, bleaching or detergent compositions according to the present invention can contain components other than the diacyl peroxide and the inorganic percompound. Conventionally components are selected from detergent builders, diluent salts, surfactants and minor proportions of colours, perfumes, bleach stabilisers, optical brighteners, soil antiredeposition agents, enzyme, dedusting agents, tarnish inhibitors and abrasives.

Suitable builder salts can be either organic, for example aminopolycarboxylates, organic polyphosphates, sodium citrate or sodium gluconate, or inorganic, for example, alkali metal carbonates, silicates, phosphates, polyphosphates or aluminosilicates. Typically, builders are present in proportions of from 1% to 90% by weight. Such compounds alter the pH of detergent/bleaching solutions. Preferably sufficient builder salt is used to adjust the pH of the solution to from pH 7 to 11, more preferably from pH 8 to 11.

A typical processing aid is sodium sulphate which is conveniently incorporated in detergent/bleaching compositions in an amount of from 1 to 40% by weight.

Where some builder salt or processing aid has been used to desensitise the diacyl peroxide the amount so used to included in the total amount of builder salt or processing aid present in the composition.

The surfactants may conventionally be water-soluble anionic, non-ionic, ampholytic or zwitterionic suface active agents. Suitable surfactants are often selected from fatty acids and their alkali metal salts, alkyl sulphonates, especially linear alkyl benzene sulphonates, sulphated aliphatic olefins, sulphated condensation products of aliphatic amides and quaternary ammonium compounds. The surfactants are normally present in the detergent composition in amounts of from 1% to 90% by weight, often in a weight ratio to the builder salts of from 2:1 to 1:10. It is believed that in aqueous alkaline media organic peroxyacids are formed from the diacyl peroixde. Consequently, the bleaching composition can include any compound or compounds which enhance the bleaching or washing activity of organic peroxyacids, such as ketones and aldehydes as described in U.S. Pat. No. 3,822,114 or certain quaternary ammonium salts as described in British Pat. No. 1,378,671, both patents to Proctor & Gamble.

One convenient method of providing a diluent/peroxyacid or precursor suitable for incorporation in a detergent composition and substantially isolated from alkaline surfactants is to form a mixture of particulate peroxyacid or precursor with a particulate inorganic diluent such as sodium sulphate or tripolyphosphate or magnesium sulphate into tablets or extrudates. Such tablets or extrudates by themselves effectively reduce the surface of the precursor or peroxyacid presented to the alkaline surfactants, and thus alleviate the problem of loss of active oxygen during storage. The problem can be further alleviated by providing an outer layer around the tablets or extrudates comprising at least one of the coating compounds described hereinbefore, generally in an amount of up to 20% by weight. Alternatively any suitable organic compounds described hereinbefore may be formed into a flexible sachet within which a diluent/peroxyacid or precursor mixture can be placed. Advantageously the tablet or extrudate, or sachet can also contain the persalt if generation of perhydroxyl anions is required in a mole ratio to the precursor of from 2:1 to 1:2, and preferably approximately 1:1, assuming one perhydrolysable site per precursor molecule.

The aliphatic peroxyacids described herein can in general be prepared by appropriate oxidation of the corresponding acyl chloride or anhydride. Gentle oxidation of an anhydride with hydrogen peroxide in ether produces a carboxy group ortho to a peroxycarboxy group, at reflux temperature. By carrying out the reaction between the acyl chloride and hydrogen peroxide in non aqueous systems such as methane sulphonic acid substantially all the acyl chloride group present in the molecule can be oxidised to peroxycarboxy groups. Thus, for example 2-peroxycarboxycyclohexanecarboxylic acid can be formed by reacting cis or trans cyclohexane-1,2-dicarboxylic anhydride with excess hydrogen peroxide in ether solution at reflux temperature for about 1.5 hours. The aqueous layer is washed with ether to extract organic compounds. The ether fractions are combined, washed with saturated ammonium sulphate solution, dried with magnesium sulphate and evaporated to dryness leaving a white solid which is the product.

Acyl peroxides, in general, can be formed by reacting hydrogen peroxide with the appropriate acyl chloride or anhydride, under such conditions that an intermediate reacts with a second acyl chloride or anhydride molecule. Thus, for example, 2,2'-dicarboxydicyclohexanoyl peroxide can be formed by reacting particulate cis or trans cyclohexane-1,2-dicarboxylic anhydride with hydrogen peroxide employing substantially the minimum amount of liquid in which to suspend the cyclohexane-1,2-dicarboxylic anhydride, at a pH of about 2 and at a temperature of about 40° C.

Preferably the peroxyacids and peroxides are formed in the presence of diluents described hereinbefore, so that at no stage is pure active oxygen containing product isolated.

Specific embodiments of the present invention will now be described more fully by way of example.

The effectiveness of bleaching compositions according to the present invention was compared with conventional inorganic persalts in washing stained fabrics with 1 liter water containing 4 gms of a detergent composition comprising linear alkyl benzene sulphonate 15%, sodium tripolyphosphate 37% sodium silicate 6%, coconut monoethanolamide 3%, sodium carboxy methylcellulose 1.5%, water 6% and balance sodium sulphate, the %s being by weight, and sufficient active oxygen-containing compounds to yield 35 ppm active oxygen in solution. The washing was carried out at a temperature in the range of 30 to 60° C. and at a pH of 9. The oxygen-containing compounds consisted of (a) sodium perborate tetrahydrate, (included for comparison) (b) 2-peroxycarboxycyclohexanecarboxylic acid and (c) 2-peroxycarboxycyclohex-3-enecarboxylic acid. The fabrics comprised cotton or polyester cotton mixtures, and the stains were conventional household stains. The stain removal was measured and broadly it was found that (b) and (c) performed substantially the same and better than (a) in the temperature range of 30 to 60° C. The washing tests were repeated using the diacyl peroxide analogues of respectively (b) and (c) together with sodium perborate tetrahydrate in a 1:1 mole ratio instead of (b) and (c). Broadly, it was found that the diacyl peroxide/persalt mixtures were also better than sodium perborate in the temperature range of 30 to 60° C. and similar to the peroxyacid themselves.

We claim:

1. A bleaching or detergent composition comprising a surfactant, a builder salt and a bleaching agent, said bleaching agent is selected from the group consisting of
acylperoxides capable of generating an aliphatic peroxyacid or anion thereof in aqueous solution, if necessary in conjunction with a persalt, said aliphatic peroxyacid being selected from the group consisting of:

(i) a peroxyacid having the general formula

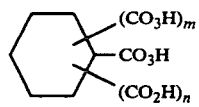

wherein
$0 \leq m \leq 5$
$0 \leq n \leq 5$ and
$m + n \geq 1$ (ii) mono and diethylenically unsaturated derivatives of said peroxyacid and (iii) nitro, chloro and lower alkyl substituted derivatives of said peroxyacid and of said mono and diethylenically unsaturated derivatives of said peroxyacid.

2. A composition according to claim 1 wherein the aliphatic peroxyacid is saturated.

3. A composition according to claim 1 wherein n = 1 and m = 0 in the general formula.

4. A composition according to claim 3 wherein the carboxy group is vicinal to the peroxycarboxy group.

5. A composition according to claim 1 wherein m = 1 and n = 0 in the general formula.

6. A composition according to claim 1 containing a persalt in a ratio of from 5 to 0.2 molecules per acyl peroxide linkage.

7. A composition according to claim 1 further comprising at least one detergent adjunct selected from the group consisting of colors, perfumes, bleach stabilizers, optical brightening agents, soil antiredeposition agents, enzymes, dedusting agents, tarnish inhibitors and abrasives.

8. A composition according to claim 1 further comprising a member selected from the group consisting of sodium sulphate and magnesium sulphate.

9. A composition according to claim 1 further comprising a desensitizing diluent in intimate contact with said bleaching agent.

10. A composition according to claim 1 wherein said bleaching agent bears a coating of a coating agent to reduce destructive interaction, during storage, between said bleaching agent and other components of the composition.

11. A composition suitable for mixing with a surfactant to form a heavy duty detergent composition, said composition comprising a bleaching agent in intimate contact with a desensitizing amount of a desensitizing diluent selected from the group consisting of detergent builders, said bleaching agent being selected from the group consisting of
acylperoxides capable of generating an aliphatic peroxyacid or anion thereof in aqueous solution, if necessary in conjunction with a persalt, said aliphatic peroxyacid being selected from the group consisting of:

(i) a peroxyacid having the general formula

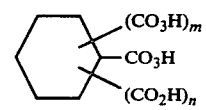

wherein
$0 \leq m \leq 5$
$0 \leq n \leq 5$ and
$m + n \geq 1$ (ii) mono and diethylenically unsaturated derivatives of said peroxyacid and (iii) nitro, chloro and lower alkyl substituted derivatives of said peroxyacid and of said mono and diethylenically unsaturated derivatives of said peroxyacid.

12. A composition suitable for mixing with a surfactant to form a heavy duty detergent composition, said composition comprising a bleaching agent in intimate contact with a desensitizing amount of a desensitizing diluent selected from the group consisting of sodium sulphate and magnesium sulphate, said bleaching agent being selected from the group consisting of acyl peroxides capable of generating an aliphatic peroxyacid or anion thereof in aqueous solution, if necessary in conjunction with a persalt, said aliphatic peroxyacid being selected from the group consisting of:

(i) a peroxyacid having the general formula

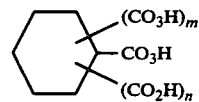

wherein
$0 \leq m \leq 5$
$0 \leq n \leq 5$ and
$m + n \geq 1$ (ii) mono and diethylenically unsaturated derivatives of said peroxyacid and (iii) nitro, chloro and lower alkyl substituted derivatives of said peroxyacid and of said mono and diethylenically unsaturated derivatives of said peroxyacid.

13. A process for bleaching comprising the steps of dissolving a bleaching agent in an aqueous solution, thereafter bringing the aqueous solution into contact with an article to be bleached at a temperature of at least ambient, maintaining contact between the bleaching agent and said article until at least some bleaching has occurred, and thereafter separating the aqueous solution from the article, said bleaching agent being selected from the group consisting of:
acylperoxides capable of generating an aliphatic peroxyacid or anion thereof in aqueous solution, if necessary in conjunction with a persalt, said aliphatic peroxyacid being selected from the group consisting of:

(i) a peroxyacid having the general formula

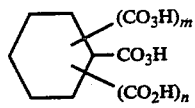
wherein
$0 \leq m \leq 5$
$0 \leq n \leq 5$ and
$m + n \geq 1$
(ii) mono and diethylenically unsaturated derivatives of said peroxyacid and
(iii) nitro, chloro and lower alkyl substituted derivatives of said peroxyacid and of said mono and diethylenically unsaturated derivatives of said peroxyacid.
* * * * *